(12) United States Patent
Brownlee

(10) Patent No.: US 11,337,869 B2
(45) Date of Patent: May 24, 2022

(54) REPLACEABLE ABSORBENT CHANNEL DIAPER FOR USE AS A MULTIPLIER WITH SINGLE-USE DISPOSABLE DIAPERS OR RE-USABLE RECYCLABLE OUTER SHELL

(71) Applicant: James Roy Brownlee, West Vancouver (CA)

(72) Inventor: James Roy Brownlee, West Vancouver (CA)

( * ) Notice: Subject to any disclaimer, the term of this patent is extended or adjusted under 35 U.S.C. 154(b) by 718 days.

(21) Appl. No.: 16/098,267

(22) PCT Filed: May 2, 2017

(86) PCT No.: PCT/CA2017/050534
§ 371 (c)(1),
(2) Date: Nov. 1, 2018

(87) PCT Pub. No.: WO2017/190237
PCT Pub. Date: Nov. 9, 2017

(65) Prior Publication Data
US 2019/0117471 A1    Apr. 25, 2019

Related U.S. Application Data

(60) Provisional application No. 62/330,767, filed on May 2, 2016, provisional application No. 62/400,219, filed on Sep. 27, 2016.

(51) Int. Cl.
*A61F 13/15* (2006.01)
*A61F 13/505* (2006.01)
(Continued)

(52) U.S. Cl.
CPC ...... *A61F 13/505* (2013.01); *A61F 13/49017* (2013.01); *A61F 13/5519* (2013.01);
(Continued)

(58) Field of Classification Search
CPC ............. A61F 13/505; A61F 13/49017; A61F 13/5519; A61F 13/5633; A61F 2013/49093; A61F 2013/5055
See application file for complete search history.

(56) References Cited

U.S. PATENT DOCUMENTS 3,376,718 A    4/1968 Kahn
3,865,110 A    2/1975 Traverse
(Continued)

FOREIGN PATENT DOCUMENTS

CA    2027234         5/1991
EP    0430443 A1     6/1991
(Continued)

OTHER PUBLICATIONS

International Search Report completed May 14, 1998 on PCT Application No. PCT/CA1997/000634.
(Continued)

*Primary Examiner* — Jacqueline F Stephens
(74) *Attorney, Agent, or Firm* — Oyen Wiggs Green & Mutala LLP

(57) ABSTRACT

A multi-piece diapering system is based on a removable, disposable absorbent channel insert diaper having hydrophobic interior leg gathers and a water impermeable backer, but without waist tabs or bands or elastic to secure the channel to the user and optionally without leg cuffs. The absorbent channel insert may be used in a single-use disposable diaper to allow such disposable diaper to be re-used multiple times by replacing the channel insert diaper when soiled. The absorbent channel insert diaper may also be used with underwear as the supporting shell, or with other exterior diaper shells or base layer diapers.

9 Claims, 15 Drawing Sheets

(51) Int. Cl.
  *A61F 13/551* (2006.01)
  *A61F 13/49* (2006.01)
  *A61F 13/56* (2006.01)
(52) U.S. Cl.
  CPC  *A61F 13/5633* (2013.01); *A61F 2013/49093* (2013.01); *A61F 2013/5055* (2013.01)

(56) References Cited

U.S. PATENT DOCUMENTS

| | | | |
|---|---|---|---|
| 3,927,674 A | 12/1975 | Schaar | |
| 4,034,760 A | 7/1977 | Amirsakis | |
| 4,085,753 A | 4/1978 | Gellert | |
| 4,493,713 A | 1/1985 | Izzo | |
| 4,496,359 A | 1/1985 | Pigneul | |
| 4,496,360 A | 1/1985 | Joffe et al. | |
| 4,578,073 A | 3/1986 | Dysart et al. | |
| 4,579,556 A | 4/1986 | McFarland | |
| 4,596,568 A | 6/1986 | Flug | |
| 4,597,760 A * | 7/1986 | Buell | A41B 13/04 604/397 |
| 4,597,761 A | 7/1986 | Buell | |
| 4,604,096 A | 8/1986 | Dean et al. | |
| 4,743,240 A | 5/1988 | Powell | |
| 4,834,737 A | 5/1989 | Khan | |
| 4,923,455 A | 5/1990 | Dean et al. | |
| 4,931,052 A | 6/1990 | Feldman | |
| 4,964,857 A | 10/1990 | Osborn | |
| 4,968,312 A | 11/1990 | Khan | |
| 5,071,414 A | 12/1991 | Elliott | |
| 5,141,505 A | 8/1992 | Barrett | |
| 5,217,447 A | 7/1993 | Gagnon | |
| 5,304,158 A | 4/1994 | Webb | |
| 5,325,543 A | 7/1994 | Allen | |
| 5,360,422 A | 11/1994 | Brownlee et al. | |
| 5,405,342 A | 4/1995 | Roessler et al. | |
| 5,409,476 A | 4/1995 | Coates | |
| 5,458,591 A | 10/1995 | Roessler et al. | |
| 5,476,457 A | 12/1995 | Roessler et al. | |
| 5,613,959 A | 3/1997 | Roessler et al. | |
| 5,778,110 A | 7/1998 | Furuya | |
| 5,853,405 A | 12/1998 | Surprise | |
| 6,015,935 A | 1/2000 | LaVon et al. | |
| 6,193,702 B1 | 2/2001 | Spencer | |
| 6,229,061 B1 | 5/2001 | Dragoo et al. | |
| 6,254,583 B1 | 7/2001 | Coates | |
| 6,450,996 B1 | 9/2002 | Otsubo | |
| 6,575,951 B1 | 6/2003 | Ono et al. | |
| 6,579,273 B2 | 6/2003 | Dupuy | |
| 6,600,086 B1 | 7/2003 | Mace et al. | |
| 6,605,071 B1 | 8/2003 | Gray et al. | |
| 6,620,145 B2 | 9/2003 | Nakaoka et al. | |
| 6,623,466 B1 | 9/2003 | Richardson | |
| 6,689,113 B2 | 2/2004 | Boulanger | |
| 6,723,080 B1 | 4/2004 | Habib et al. | |
| 6,764,477 B1 | 6/2004 | Chen et al. | |
| 6,926,705 B1 | 8/2005 | Coates | |
| 6,932,800 B2 | 8/2005 | LaVon et al. | |
| 6,989,005 B1 | 1/2006 | LaVon et al. | |
| 6,989,006 B2 | 1/2006 | LaVon et al. | |
| 7,166,095 B1 | 1/2007 | Coates | |
| 7,264,615 B2 | 9/2007 | Sherrod et al. | |
| 7,431,716 B2 | 10/2008 | Tracy | |
| 7,491,196 B2 | 2/2009 | Franke et al. | |
| 8,569,380 B2 | 10/2013 | Brownlee | |
| 2002/0029546 A1 | 3/2002 | Gould | |
| 2002/0065500 A1 | 5/2002 | Rossi | |
| 2003/0111168 A1 | 6/2003 | Olson et al. | |
| 2003/0196250 A1 | 10/2003 | Gadot et al. | |
| 2003/0199844 A1 | 10/2003 | LaVon et al. | |
| 2004/0078017 A1 | 4/2004 | Koyama et al. | |
| 2004/0122401 A1 | 6/2004 | Van Gompel et al. | |
| 2004/0264815 A1 | 12/2004 | Gibeau | |
| 2005/0049569 A1 | 3/2005 | Tracy | |
| 2005/0210560 A1 | 9/2005 | Coates | |
| 2005/0215968 A1 | 9/2005 | Henderson | |
| 2010/0179497 A1 * | 7/2010 | Brownlee | C07K 11/02 604/385.14 |
| 2010/0179500 A1 | 7/2010 | Roe et al. | |
| 2012/0022492 A1 | 1/2012 | Roe et al. | |
| 2012/0123366 A1 | 5/2012 | Brownlee | |
| 2014/0257231 A1 | 9/2014 | Wang et al. | |

FOREIGN PATENT DOCUMENTS

| | | |
|---|---|---|
| EP | 0667136 A1 | 8/1995 |
| EP | 0684029 A2 | 11/1995 |
| EP | 0763353 A2 | 3/1997 |
| GB | 1151321 | 5/1969 |
| GB | 2103930 | 3/1983 |
| GB | 2142541 | 1/1985 |
| GB | 2148095 | 5/1985 |
| GB | 2302026 | 1/1997 |
| GB | 2322288 A | 8/1998 |
| GB | 2410439 | 8/2005 |
| JP | 2014147424 A | 8/2014 |
| WO | 85/03430 A1 | 8/1985 |
| WO | 93/23000 A1 | 11/1993 |
| WO | 94/03137 A1 | 2/1994 |
| WO | 94/15563 | 7/1994 |
| WO | 96/29037 A1 | 9/1996 |
| WO | 97/18785 | 5/1997 |
| WO | 99/12502 A1 | 3/1999 |
| WO | 2005/072554 A1 | 8/2005 |
| WO | 2008/014621 A1 | 2/2008 |
| WO | 2008/095310 A1 | 8/2008 |
| WO | 2010/078661 A1 | 7/2010 |

OTHER PUBLICATIONS

International Search Report completed Oct. 16, 2007 on PCT Application No. PCT/CA2007/001370.
International Search Report completed Apr. 9, 2008 on PCT Application No. PCT/CA2008/000257.
Guardian Unlimited, "Is biodegradable all it's cracked up to be?" by Lucy Siegle, May 28, 2006, http://observer.guardian.co.uk/magazine/story/0,,1782933,00.html. (4).
World Centric, "Compostable, Biodegradable BioPlastics", 2007, http://www.worldcentric.org/store/bioplastics.htm (5).
Food productiondaily.com-europe, "Bioplastics demand experiencing boom in Europe" by AhmedElamin, 2006, http://www.foodproductiondaily.com/news/printNewsBis.asp?id=72306 (6).
BPIWorld.org, "Approved Products—Compostable Bags & Films", 2006, http://www.bpiworld.org/BPI-Public/Approved/1.html (7).
BPIWorld.org, "Approved Products—Resins", 2007, http://www.bpiworld.org/BPI-Public/Approved/3.html (8).
BPIWorld.org, "Approved Products—Foodservice and Packaging", 2007, http://www.bpiworld.org/BPI-Public/Approved/2.html (9).
ASTM International, Designation: D 6400-04, "Standard Specification for Compostable Plastics", 3 pages, 2006. (10).
ASTM International, Designation: D 6002-96 (Reapproved 2002), "Standard Guide for Assessing the Compostability of Environmentally Degradable Plastics", 2002, 15 pages, http://www.mindfully.org/Plastic/Biodegrade/Compostability-Degradable-Plastics1mar02.htm (11).
International Search Report completed Apr. 1, 2010 on PCT Application No. PCT/CA2010/000050.
International Search Report completed Dec. 13, 1993 on PCT Application No. PCT/US93/07228.
International Search Report completed Jul. 31, 2017 on PCT Application No. PCT/CA2017/050534.
European Patent Office Supplementary Search Report completed Nov. 1, 2013 on European Patent Application No. EP07785033.
Extended European Search Reported dated Mar. 2, 2020 issued on EP Application No. EP 17 79 2328.

* cited by examiner

REPLACEABLE ABSORBENT CHANNEL DIAPER FOR USE AS A MULTIPLIER WITH SINGLE-USE DISPOSABLE DIAPERS OR RE-USABLE RECYCLABLE OUTER SHELL

CROSS REFERENCE TO RELATED APPLICATION

The present application claims the benefits, under 35 U.S.C. § 119(e), of U.S. Provisional Application Ser. No. 62/330,767 filed May 2, 2016 entitled "Replaceable Absorbent Diaper Channel For Use With Re-usable Outer Shell In Two-Piece Disposable Diapering Systems" and U.S. Provisional Application Ser. No. 62/400,219 filed Sep. 27, 2016 entitled "Replaceable Absorbent Diaper Channel For Use As A Multiplier With Single-Use Disposable Diapers", which are incorporated herein by this reference.

TECHNICAL FIELD

The invention relates to the construction of infant or adult diapers, and particularly to multi-piece diapers having re-usable and/or disposable components, to disposable diapers having a re-usable, washable shell and a replaceable absorbent element and to disposable absorbent inserts for use with single-use disposable diapers.

BACKGROUND

Conventionally, infant diapers have been one of two types, either washable cloth diapers or disposable diapers of synthetic materials. Parents who are environmentally responsible would prefer to use diapers for their infants which are washable and reusable. Cloth diapers are intended to have a useful life greater than the typical period of time from the birth of an infant to when the infant no longer requires diapers, so that no replacements are required. However, machine washable cloth diapers are expensive, and require significant time, labor and energy to wash them. Therefore despite the best intentions of many parents, due to the time and work involved in washing diapers, the vast majority of parents, either from the outset or very soon afterwards use single-use disposable diapers. A further factor is that the initial expense of purchasing good quality fitted washable cloth diapers is quite high compared to the initial cost of disposable diapers.

Currently therefore the vast majority of infant diapers purchased are of the single-use disposable variety. Existing single-use disposable diapers have a liquid impervious outer layer, an inner non-woven liner and an integral layer of absorbent material, typically pulp fluff and/or super-absorbent polymers (SAP), sandwiched between the inner and outer layers. Standard disposable diapers are not re-usable and cannot be economically recycled. They create a large volume of waste, since the entire garment is disposed of in landfill after a single use. If the diaper is wetted or soiled even slightly, the entire diaper is discarded, at considerable expense and causing considerable waste. There has therefore been a longstanding need for an infant diaper design which reduces the amount of waste by providing parents with greater opportunity to choose to re-use single-use diapers multiple times or to wash and re-use components of a disposable diaper system.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with articles, systems and methods which are meant to be exemplary and illustrative, not limiting in scope. In various embodiments, one or more of the above-described problems have been reduced or eliminated, while other embodiments are directed to other improvements.

The present inventor has discovered that by using a disposable insert which takes the form of a diaper channel formed like a disposable diaper in that it has a channel formed by interior leg gathers, but unlike a disposable diaper in having no waist tabs or waist band, and optionally no leg cuffs, the parent can convert a single-use diaper into a multiple-use diaper. Such a disposable diaper insert is referred to herein as a "channel insert diaper". The channel insert diaper disclosed herein forms one part of a two- or three-piece diaper system and is intended for insertion into a reusable, washable exterior shell such as undergarments, under shorts or other clothing, or a disposable shell as disclosed herein (any of the foregoing which is referred to hereafter as an "exterior shell"), or an absorbent diaper, which is referred to herein as a "base layer diaper" which may be a single-use disposable diaper, or a cloth diaper, swim diaper, training diaper, adult incontinence diaper, gPants™ or a pull-up diaper. The channel insert diaper converts an exterior shell or base layer diaper to a multiple-use diaper, and is both removable and replaceable. It is disposable after soiling. It has three major components: (i) a waterproof exterior shell which may be provided on the outer surface thereof with glue strips, (ii) hydrophobic interior leg gathers attached to both sides, and (iii) a central absorbent pad that preferably utilizes super thin core technology.

The disclosed diaper system using a channel insert diaper can thereby convert a single-use disposable diaper into a multiple-use, reusable, disposable diaper. The disclosed diaper system may be provided by using one disposable non-replaceable, non-removable, absorbent diaper as a base layer diaper plus one or a plurality of replaceable, removable, absorbent channel insert diapers.

The interior leg gathers provided on the channel insert diaper may be the same or similar in construction to those on a single-use disposable diaper. However the base layer diaper need not have interior leg gathers, for example where the base layer diaper is a cloth diaper. The channel insert diaper may be provided with high interior leg gathers and a waterproof outer shell with or without releasable exterior glue strips to hold it in place when inserted in a base layer diaper or exterior shell.

Using the present invention to provide a multiple-use disposable diaper can cut the cost of disposable diapering since the cost of manufacturing and shipping the channel insert diaper will generally be less than the cost of the complete single-use diaper. In that case every time a parent only uses a channel insert diaper for a diaper change and reuses the single-use diaper as the base layer diaper she/he can reduce the cost of diaper use. Where the base layer diaper is a standard single-use disposable diaper it may serve as a last diaper change and can be used without the channel insert diaper and disposed of after such last use. Thus the parent can always have the option of using the single-use diaper without a channel insert diaper as a last diaper change for the single-use diaper. This can arise for example where the Velcro™ tabs on the base layer single-use diaper are reaching the end of their useful life.

Thus when a parent reuses either an exterior shell or a base layer diaper such as a single-use disposable diaper in combination with a channel insert diaper instead of only using single-use disposable diapers, she/he can reduce both the carbon footprint and the landfill waste volume created by the use on its own of the single-use disposable diaper. The amount of carbon footprint and landfill reduction may therefore be controlled and determined by the individual parent. This varies depending on the number of channel insert diapers she/he uses with the single-use disposable diaper as a base layer diaper. Therefore both the carbon footprint and the landfill waste reduction can be increased in proportion to the number of channel insert diaper replacements a parent uses.

Current super thin absorbent core technology for single-use disposable diapers may also be used in the channel insert diaper's absorbent core to minimize its thickness and increase the comfort for the baby. For example, the absorbent centre core pad thickness of the channel insert diaper may be selected to be less than ½ inch (12.5 mm) for maximum comfort and environmental impact. While using super thin absorbent core technology for both the single-use diaper and channel insert diaper minimizes bulkiness, and the baby's comfort and coolness, in some cases the parent may consider that a standard single-use diaper using thick pulp fluff material is more comfortable for the infant, while using the super thin absorbent core technology for the channel insert diaper's absorbent pad to make the overall thickness of the diaper system manageable. Or the opposite could be selected by the parent, using thin single-use diapers with super thin absorbent core technology for the base diaper layer while using thicker absorbency in the channel insert diaper for comfort against the infant's skin.

The channel insert diaper is preferably the same, or narrower in width than the central channel of the exterior shell or channel in the base layer diaper but can also be wider. Similarly the inserted channel insert diaper is the same or shorter in length than the central longitudinal length of the base layer diaper's central absorbent channel or the exterior shell's central channel when attached or glued to the exterior shell or base layer diaper but may be longer. The inserted channel insert diaper may have the same construction as the absorbent channel of the single-use disposable diaper absorbent channel which forms the base layer diaper, with interior leg gathers, but the inserted channel insert diaper may also have different construction not identical to the base layer diaper. Preferably the channel insert diaper is a diaper channel that can be produced on the same diaper machines as a single-use disposable diaper.

With respect to performance characteristics, the channel insert diaper that fits into the single-use disposable base layer diaper may have the same performance qualities and channel capacity as the channel of the base layer diaper, but those characteristics may also be greater or lesser.

The channel insert diaper therefore provides a diaper multiplier for use in either a base layer diaper or an exterior shell. This differs from current diaper pads or doublers or other type of flow-through products. Unlike a "diaper doubler", the channel insert diaper disclosed herein is not designed to increase the absorbent capacity of any absorbent channel of a single-use diaper. Rather it is designed to increase the number of times a single-use diaper can be used. Hence it is a diaper multiplier, not a diaper doubler. It can provide a super thin super absorbent diaper channel which is a disposable single-use product that can be added to a single-use disposable diaper, a cloth diaper or other base layer diaper, and/or a non-absorbent diaper shell. The disclosed single-use channel insert diaper can convert existing single-use disposable diaper products into a multiple-use diaper system by inserting, removing and replacing the channel insert diaper.

The channel insert diaper has a waterproof exterior layer to prevent the base layer diaper or the waterproof diaper shell, that it is inserted into, from getting wet or soiled. The absorbent channel of a single-use diaper is thereby kept clean and dry by the waterproof layer and hydrophobic leg gathers of the channel insert diaper. The absorbent pulp and/or SAP of the base layer diaper's absorbent layer may serve to stabilize the single-use diaper to permit the channel insert diaper to be more readily inserted. The channel insert diaper has hydrophobic interior leg gathers on each lateral side of its central channel. These interior leg gathers keep the interior leg gathers of a single-use disposable diaper dry when the channel insert diaper is used in a single-use disposable diaper.

The channel insert diaper may be provided with glue strips on the bottom of the waterproof outer layer to hold the channel insert diaper in place in the exterior shell or base layer diaper, such as a single-use diaper, however such glue strips are optional as they are not necessary for the functioning of the channel insert diaper.

The channel insert diaper is preferably manufactured in various lengths, widths and thicknesses which conform to fit into standard sizes of the popular brands of single-use disposable diapers with different dimensions. The size of the channel insert diaper will therefore vary with corresponding base layer diaper sizes.

Multiple channel insert diapers using super thin technology can be stacked one on top of the other within an exterior shell or base layer diaper to permit the parent to change the infant's diaper without needing to carry extra diapers or retrieve replacements from storage. A weak adhesive or exposed glue strips may be used between adjacent inserts. The last channel insert diaper may be left glued to the single-use diaper shell for the last diaper change for that particular single-use disposable diaper.

Thus a single-use diaper can be pre-loaded with multiple channel insert diapers at one time and then subsequently released and removed one at a time when used. Stacking two or more channel insert diapers on top of one another, or one or more channel insert diapers in combination with one or more absorbent booster pads within a base layer diaper can be done for either the convenience of use or a baby's comfort.

The present inventor has therefore devised a system for converting single-use disposable diapers to multiple-use diapers by providing a removable disposable absorbent channel insert. The insert is referred to herein as a "channel insert diaper" as it takes the form of a disposable diaper with a channel formed by interior leg gathers but no waist tabs or waist band, and optionally no leg cuffs.

According to one embodiment, an absorbent diaper channel insert is provided with hydrophobic leg gathers and a water impermeable backer, but without waist tabs, waist band or leg cuffs to secure the channel to the user. An adhesive strip may be provided on the water impermeable backer to secure the diaper channel insert in a supporting shell or diaper. The absorbent diaper channel insert may be used with a re-usable disposable, exterior non-absorbent shell or garment, or may be used in a base layer diaper such as a single-use disposable diaper to allow such disposable diaper to be re-used multiple times. The absorbent channel insert diaper may be used with underwear as the supporting shell, or with machine washable cloth diapers, swim pants, swim diapers or gPants™.

Consequently, the present invention provides a disposable channel insert diaper for multiplying the number of diaper changes to which a single-use disposable diaper can be subjected. Thus the parent can choose to reduce cost and waste by re-using a standard single-use disposable diaper. The channel insert diaper can also be used with a re-usable non-absorbent outer liquid impervious shell, having closures suitable for multiple re-uses and elasticized legs, with or without interior leg gathers. The shell may be rinsable or hand- or machine-washable. The replaceable absorbent channel insert diaper has a diaper channel with elongated elastic members secured therein to form hydrophobic leg gathers when in operative position. The absorbent diaper channel insert is thus provided with hydrophobic leg gathers and a water impermeable backer, but without waist tabs, or waist band, and optionally no leg cuffs to secure the channel to the user. An adhesive strip may be provided on the water impermeable backer to secure the channel insert diaper in the supporting shell or base layer diaper. It may be supported on the user by a re-usable non-absorbent shell constructed according to standard non-durable disposable diaper construction which is machine washable when washed. Or it may be supported by a single-use disposable diaper to allow such disposable diaper to be re-used multiple times. The absorbent channel insert diaper may also be used with underwear as the supporting shell, or with other base layer diapers such as machine washable cloth diapers, swim pants, swim diapers or gPants™.

According to one aspect of the method a parent may thereby choose to insert the removable replaceable absorbent channel insert diaper into a standard disposable diaper to reduce waste by re-using the single-use disposable diaper after the channel insert diaper has been soiled and replaced. The invention therefore provides a multi-piece diapering system based on an absorbent channel insert diaper having hydrophobic leg gathers and a water impermeable backer, but without waist tabs or leg cuffs to secure the channel to the user. One or more adhesive strips may be provided on the water impermeable backer to secure the channel insert diaper in the supporting shell. The removable, replaceable disposable absorbent channel insert diaper preferably comprises (i) a waterproof exterior outer shell which may be provided on the outer surface thereof with glue strips, (ii) a central absorbent pad that preferably utilizes super absorbent, super thin core technology, (iii) wherein the upper surface of the pad is hydrophilic and provided with hydrophobic elastic interior leg gathers extending lengthwise along either opposed edge thereof. The channel insert diaper may be constructed as a standard disposable diaper but without waist tabs or waist band to secure the channel to the user and optionally without leg cuffs.

The disclosed embodiments provide further advantages in facilitating the recycling of disposable diapers by providing multiple separate elements of the disposable diaper system. Currently suitable plastic films and absorbent pulp and SAPs all have potential applications for recycling. However due to difficulty in collecting and separating the potentially recyclable materials, recycling of disposable diapers is currently not widely accepted. The present embodiments facilitate the separation of recyclable materials from a disposable diaper system. For example, where the supporting shell is a disposable re-usable machine-washable non-absorbent diaper shell, the supporting shell and diaper channel insert may be separately collected for recycling of plastic and absorbent material. In that example where the supporting shell is without absorbent material which is exposed to contact with liquid, the exterior shell may be readily cleaned or otherwise processed for recycling. As a further example the removable, replaceable disposable absorbent diaper channel insert's absorbent pad may be made separable from the body of the diaper channel insert for ease of separating and recycling the absorbent elements of the diaper channel insert. For example the SAP may be contained in a separable absorbent packet or porous plastic pad or bag holder to facilitate separation and recycling after use so the SAP can be separated from the diaper channel insert during the recycling process.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

In drawings which disclose a preferred embodiment of the invention.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Definitions for purposes of this application:

"disposable" means a diaper component that is intended to be disposed of after a limited number of uses or a single-use, and is not intended to have a useful life comparable to the typical period of time from the birth of an infant to when the infant no longer requires diapers;

"non-disposable" means a diaper component that is intended to have a useful life comparable to the typical period of time from the birth of an infant to when the infant no longer requires diapers;

"washable" in reference to an article means that the article remains sufficiently intact for normal use after washing in a standard residential clothes washing machine or hand washing using soap and water;

"single-use disposable diaper" means a disposable diaper which must generally be disposed of for sanitary reasons after a single instance of urination or defecation by the wearer;

"channel insert diaper" means the disclosed diaper multiplier which is inserted into an exterior shell or base layer diaper to form a two-piece diaper system, and which comprises (i) a waterproof exterior outer shell, (ii) a central absorbent pad; and (iii) wherein the upper surface of the absorbent pad is hydrophilic and provided with hydrophobic elastic interior leg gathers extending lengthwise along either opposed edge thereof;

"exterior shell" means a reusable exterior shell such as undergarments, undershorts or other clothing, or a disposable shell as disclosed herein which function to hold and support the channel insert diaper in place on a diaper wearer;

"base layer diaper" means a single-use disposable diaper, or a cloth diaper, swim diaper, training diaper, adult incontinence diaper, gPants™ or pull up diaper which can be used to hold and support the channel insert diaper in place on a diaper wearer;

"interior leg gathers" means an elasticized bather to waste movement extending upwardly from the inner surface of the diaper spaced inwardly from the leg opening; and "leg cuff" means an elasticized border of a leg opening formed when the diaper is worn on the user.

Figure 1:
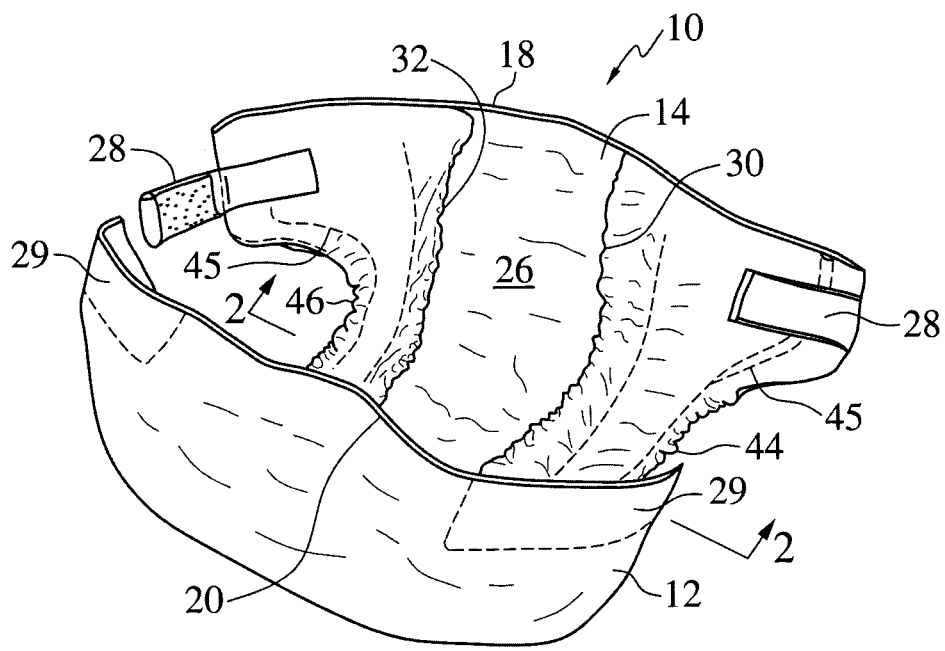
FIG. 1 is a perspective view of a conventional single-use disposable infant diaper.
Figure 2:
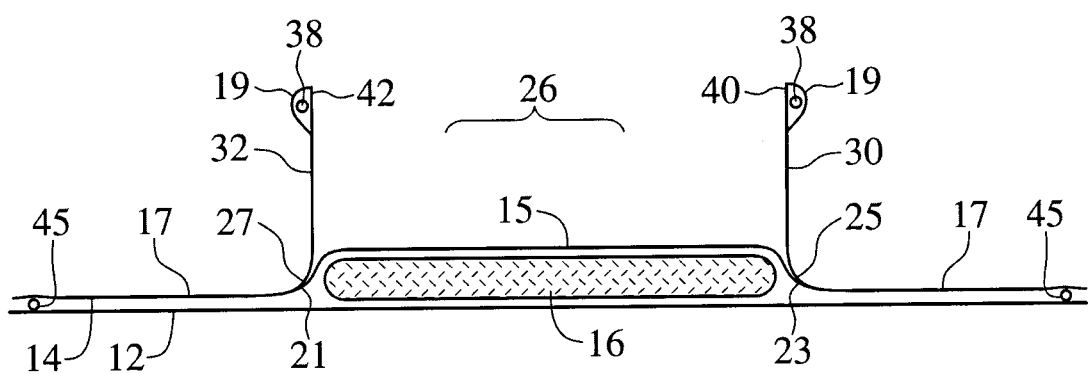
FIG. 2 is a cross-section taken along line 2-2 of FIG. 1 (not to scale)

FIGS. 1 and 2 illustrate a conventional single-use disposable diaper 10. It is constructed of an hour-glass shaped backsheet 12 made of a lightweight liquid-impervious polyethylene plastic (PE), a non-woven liner 14 made from a non-absorbent synthetic plastic such as non-woven polypropylene, and an absorbent pad 16 sandwiched between backsheet 12 and liner 14. Other conventional disposable diapers are T-shaped, with a rectangular body and a rectangular waist portion. The diaper has a back waist section 18, front waist section 20, and central area 26. Adhesive or the hook portion of Velcro™ flaps 28 are provided to attach the garment around the infant. Areas of high gloss polyethylene plastic film, or Velcro loop strips 29 are provided on backsheet 12 to which adhesive or Velcro strips 28 can releasably adhere without tearing the backsheet 12 on removal. Elasticized interior leg gathers 30, 32 are formed in the non-woven liner with elastic members 38 running along inner edges 40, 42. Outside elastic leg cuffs are provided at 44, 46 with elastic members 45 provided at their outer edges. Elastic members 38, 45 are typically thin rubber ribbons, or a hot melt elastomeric adhesive may be used as is known in the disposable diaper art.

As illustrated in FIG. 2, the non-woven liner 14 of the conventional single-use disposable diaper comprises three sections, an inner hydrophilic sheet 15 and outer hydrophobic sheets 17. Sheet 15 permits moisture to penetrate to pad 16 while keeping the skin of the infant away from the pad 16. Sheets 17 form the interior leg gathers 30, 32 which retain fecal matter and moisture in the central area 26. Absorbent pad 16 is formed of pulp fluff material which is wrapped in a thin layer of absorbent paper tissue to maintain the integrity of the pad and prevent bunching of the fluff. Crystals of super absorbent polymers are typically distributed throughout the fluff to increase the absorbency of the pad 16.

Figure 3:
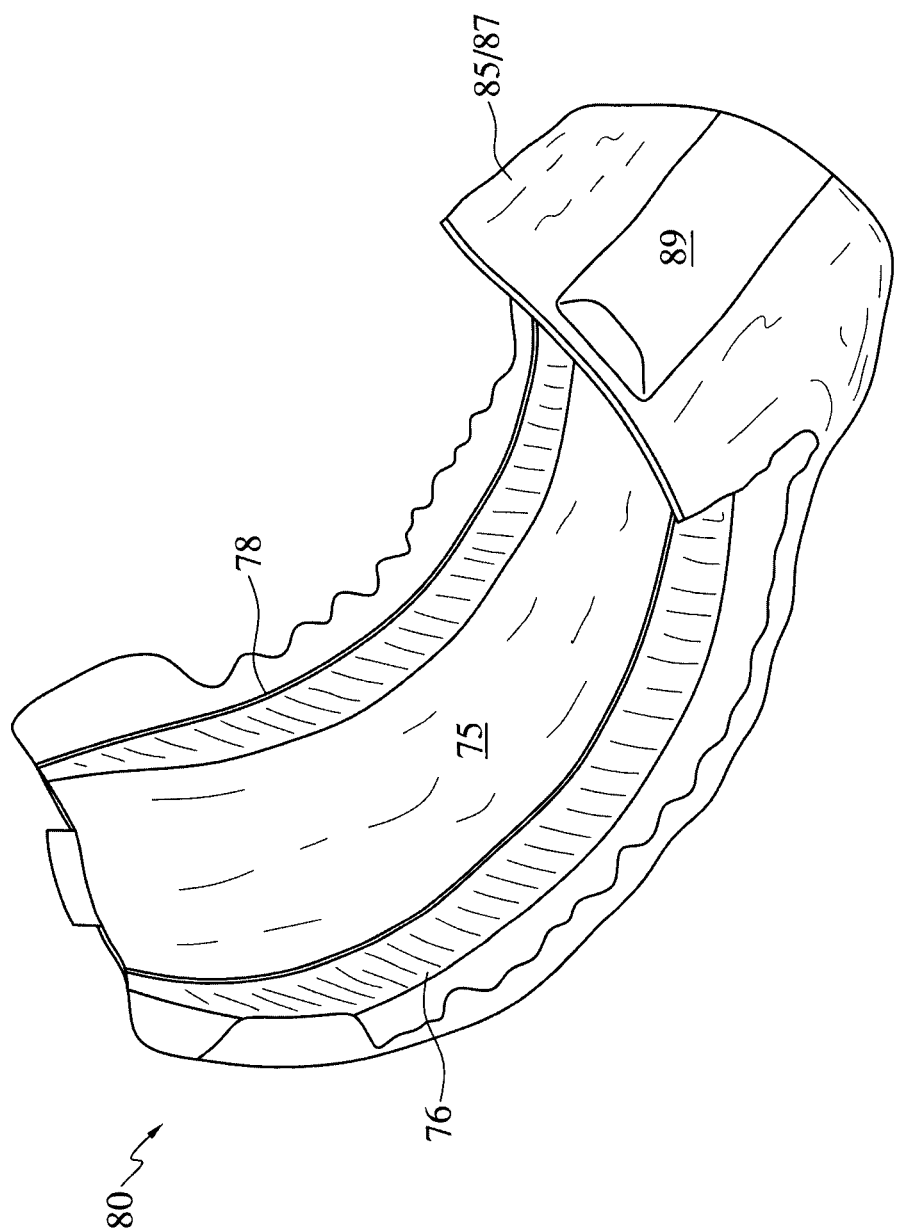
FIG. 3 is a perspective view of an embodiment of a disposable removable/replaceable absorbent channel insert diaper according to the invention.
Figure 4:
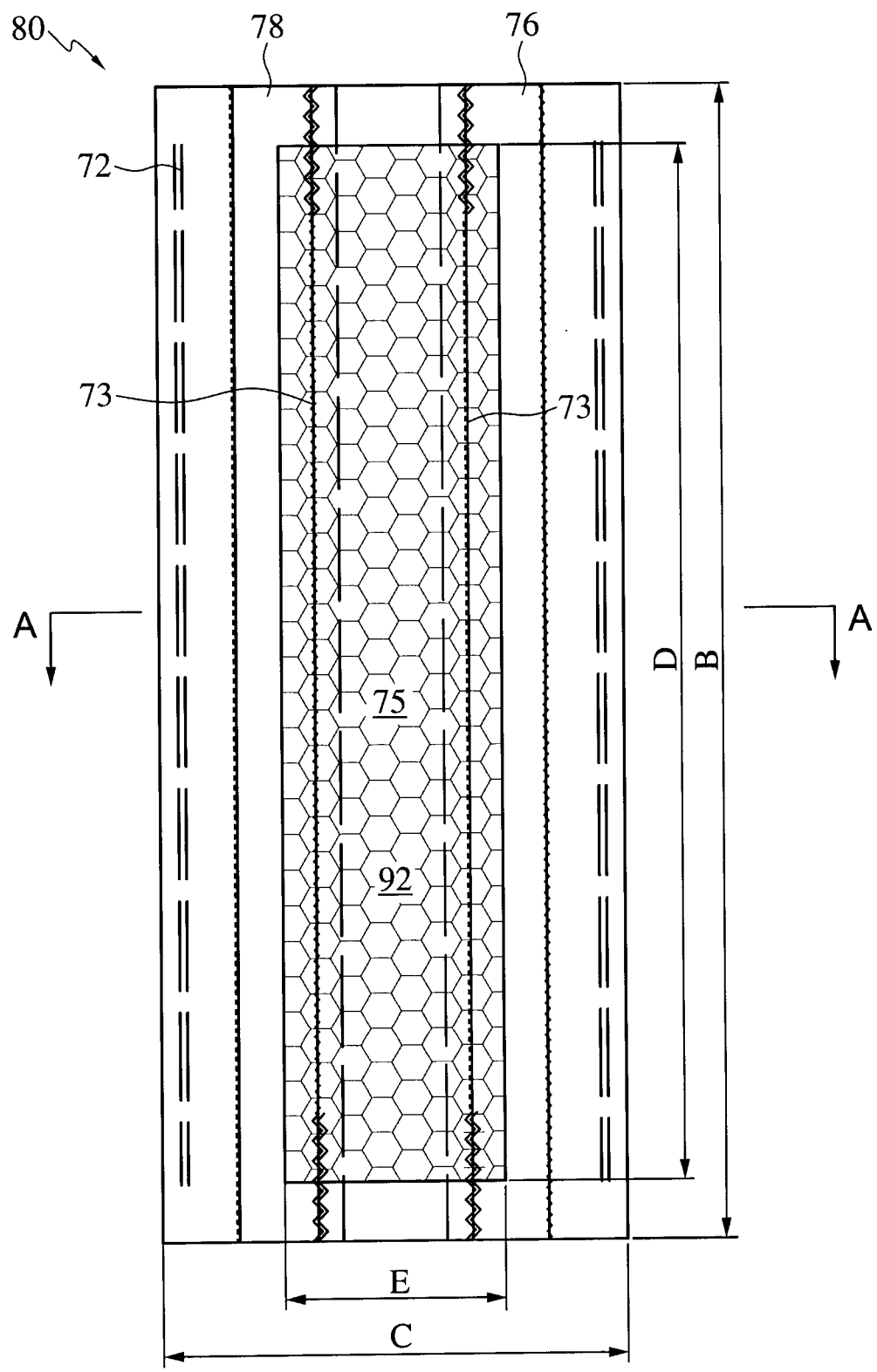
FIG. 4 is a plan view of the embodiment of the disposable removable/replaceable absorbent diaper channel shown in FIG. 3 in a flattened stretched configuration with the non-woven layer transparent to show the absorbent pad.
Figure 5:
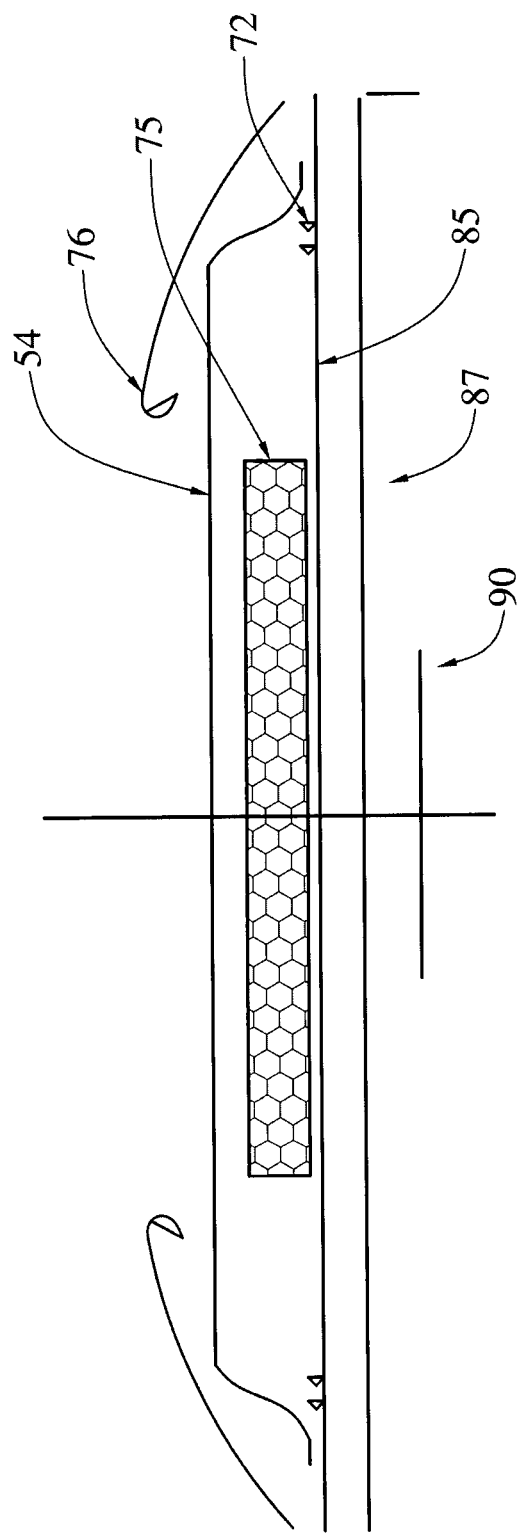
FIG. 5 is a cross-section taken along line A-A of FIG. 4 (not to scale)

FIG. 3 through 5 illustrate a first embodiment of the disposable, absorbent channel insert diaper 80 of the present invention. FIG. 3 through 5 illustrate a disposable, removable, replaceable absorbent channel insert diaper 80 (FIG. 3) which in combination with single-use disposable diaper 10 or other exterior shell or base layer diaper can provide a multi-piece diaper system, by being removably positioned and held around the user's body by single-use disposable diaper 10 or other exterior shell or base layer diaper. Absorbent channel insert diaper 80 can also be used in underwear to form an incontinent garment, or with any single-use disposable diaper to obtain multiple uses from a standard disposable diaper, or with swim diapers, swim pants or gPants™. Channel insert diaper 80 is sized to fit snugly up against leg cuffs 44, 46 in FIG. 1 or interior leg gathers 30, 32 in FIG. 1, if present in the base layer diaper 10. Channel insert diaper 80 may be a standard disposable diaper construction but without tabs or waist bands and optionally without leg cuffs. It may thus be formed in a manner similar to the conventional disposable diaper 10, using conventional machinery for manufacturing disposable diapers. Channel insert diaper 80 has an absorbent pad 75 which may be manufactured from any of the existing absorbent materials such as fluff, super-absorbent polymer (SAP), or fibrous super-absorbent polymer but is preferably an ultra-thin air-laid pulp and polyolefin web with thermally-bonded super-absorbent polymers of the type manufactured by Thermacore™. The preferred pad 75 (see FIG. 5) may be an ultra-thin absorbent pad manufactured using SAPs, such as manufactured by Drylock Technologies NV of Belgium under the brand TOUJOURS, Evonik Industries AG of Essen, Germany and others. Such air-laid pads provide greater absorbency with less material and less bulk and thickness. The absorbent pad 75 may also be SAP plus wood pulp wrapped in a layer 79 of non-woven hydrophilic material, (see FIG. 5C) with a top layer 83 of hydrophilic non-woven. SAP sheet 81 is a non-woven sheet which prevents the migration of the SAP from pad 75 to protect the infant's skin. The non-woven layers keep the skin of the infant from the upper side of the pad 75. The absorbent pad 75 is therefore absorbent on all sides of the pad 75, upper side, lower side and edges so that liquid which gets under the pad 75 when installed in an exterior shell or base layer diaper 10 is absorbed. Leg gathers 76, 78 are formed of non-woven hydrophobic material with elastic members 73 within folds 77 in the embodiments shown in FIGS. 5 and 5C.

Figure 5A:
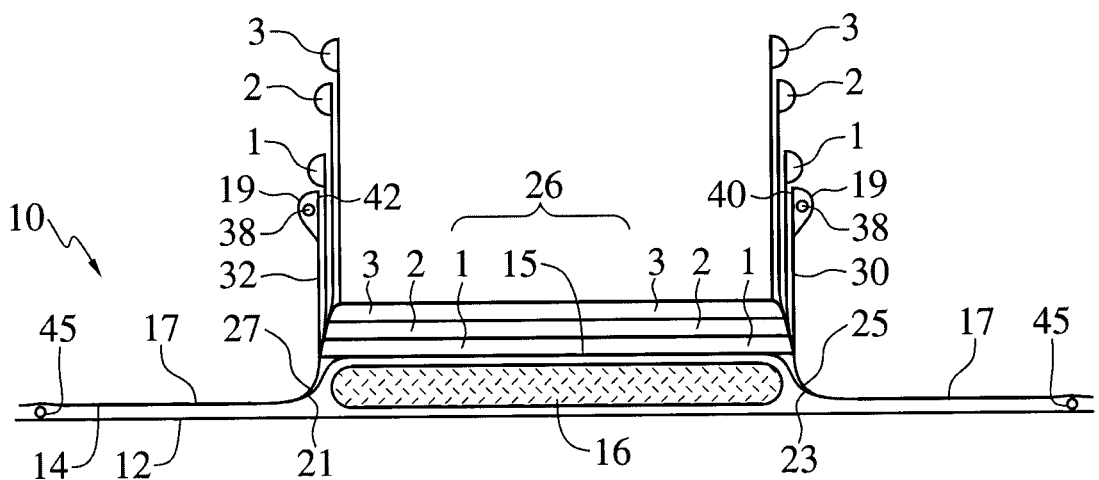
FIG. 5A is a transverse cross-section showing multiple inserts stacked in a single-use diaper (not to scale)
Figure 5B:
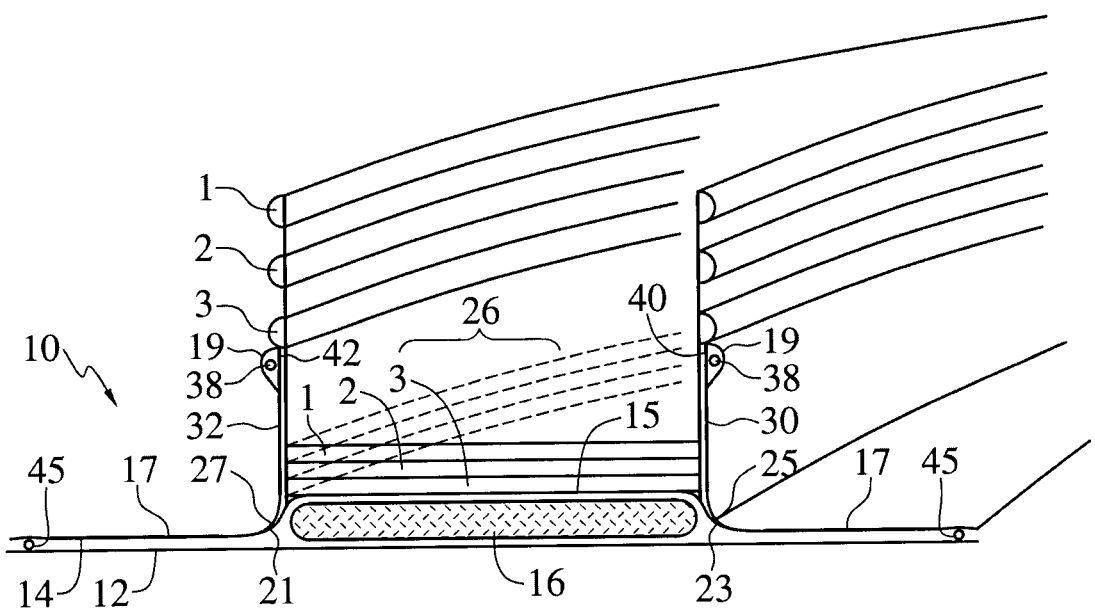
FIG. 5B is a transverse cross-section showing in perspective view multiple inserts stacked in a single-use diaper (not to scale)
Figure 5C:
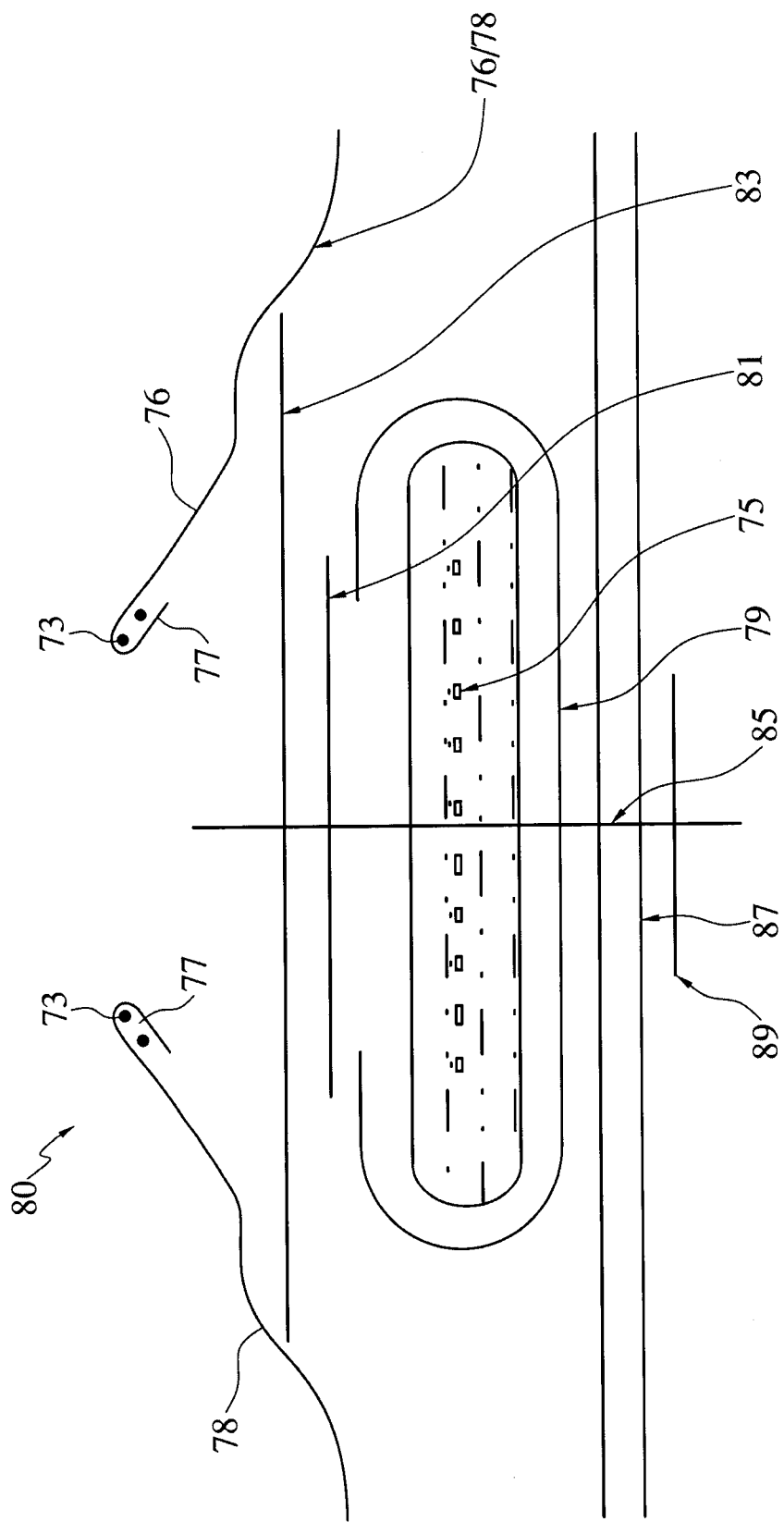
FIG. 5C is a cross-section of a second embodiment of the channel insert diaper taken along line A-A of FIG. 4 (not to scale)

Liquid-impermeable backsheet 85 is breathable PE laminated with spunbond non-woven backsheet 87 (FIG. 5C). Interior leg gathers 76, 78 are provided in the diaper channel 80 shown in FIG. 5C formed from hydrophobic non-woven sheets which incorporate elastic strips 73. The outer surface of backer sheet 85/87 may also be provided with strips of releasable adhesive 90, protected by removable paper cover release paper strips 89 until in use, in order to assist the parent in securing the channel insert diaper 80 in place. The length B of the channel insert diaper 80 may be the full length of the base layer diaper, for example from 340 mm for a newborn size to 430 mm for a large diaper. The width C of the channel insert diaper 80 may be up to the full width of the base layer diaper, for example 180 mm. The corresponding length D of the pad 75 may be from 300 mm for a newborn size to 390 mm for a large diaper. The width E of the pad 75 may be about 85 mm. The pad 75 may have an embossed surface as shown at 92.

The channel insert diaper 80 can be used in exterior shells 50 or base layer diapers (FIG. 7), including any single-use disposable diaper, swim pant, swim diaper or gPant™. It can be placed in the above-mentioned products slightly forward or backward for a female or male, using the adhesive strip 90 for placement to provide the optimum absorption performance for the wearer. A single-use disposable diaper does not permit this. The system may also use a booster pad (not shown), to insert in channel insert diaper 80 overnight for additional absorption, formed of a spunbond non-woven topsheet, absorption core of SAP and air laid, and which may also be provided with an adhesive strip protected by release paper.

Multiple channel insert diapers 80 using super thin technology can be stacked one on top of the other within an exterior shell or base layer diaper to permit the parent to change the infant's diaper without needing to carry extra channel insert diapers or retrieve replacements from storage. FIGS. 5A and 5B show in cross-section multiple inserts stacked between the interior leg gathers 30, 32 of a single-use diaper 10. Three channel insert diapers designated 1, 2 and 3 are shown stacked one on top of the other in the single-use diaper 10 with their interior leg gathers extending upwardly on the inner side of the interior leg gathers 30, 32 of the single-use diaper 10. A weak adhesive may be used between adjacent channel insert diapers to maintain them in place or the parent may expose the glue strips 89 on each insert. Thus the parent may elect to stack multiple inserts or they may come pre-packaged as a unitary stack. The last channel insert diaper 80 may be left glued to the single-use diaper shell for the last diaper change for that particular single-use disposable diaper. Thus a single-use diaper 10 can be pre-loaded with multiple channel insert diapers 80 at one time which are then released and removed one at a time when used. Stacking two or more channel insert diapers on top of one another, or one or more channel insert diapers in combination with one or more absorbent booster pads within a base layer diaper can be done for either the convenience of use or a baby's comfort.

Figure 6:
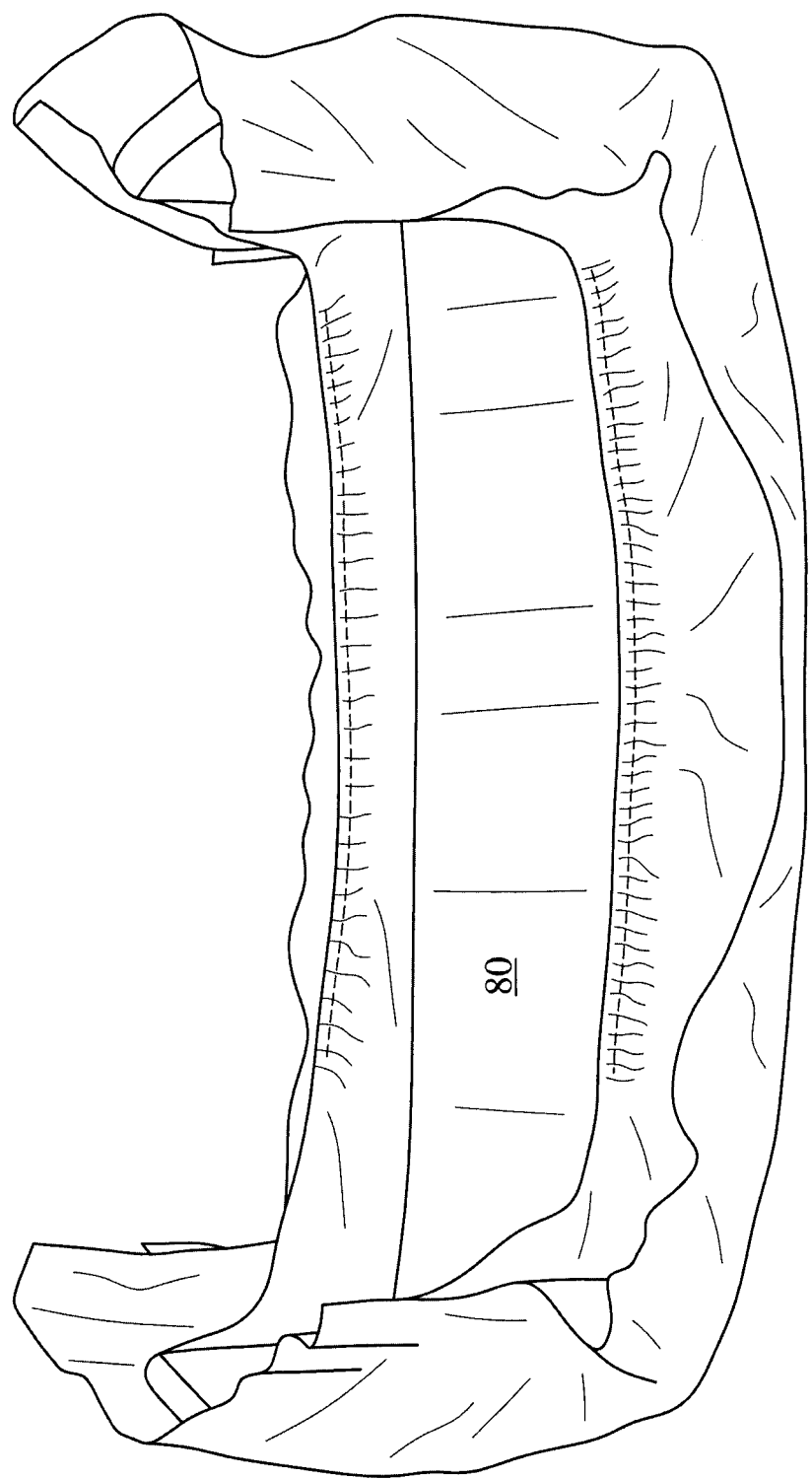
FIGS. 6-10 are perspective views illustrating the use of an embodiment of a channel insert diaper as shown in FIG. 3 in a single-use disposable diaper as shown in FIG. 1.

One manner of use of the invention is illustrated in FIG. 7-10. The exterior shell 50, single-use diaper 10 and channel insert diaper 80 may all be manufactured by the same manufacturer as separate elements and packaged and sold separately to the consumer. The channel insert diaper 80, shown laid out in FIG. 6, may be used by inserting into an existing single-use disposable diaper 10 or shell 50, or other base layer diaper or shell. Shell 50 can similarly be packaged for the consumer without a channel insert diaper 80 but rather provided separately.

Figure 7:
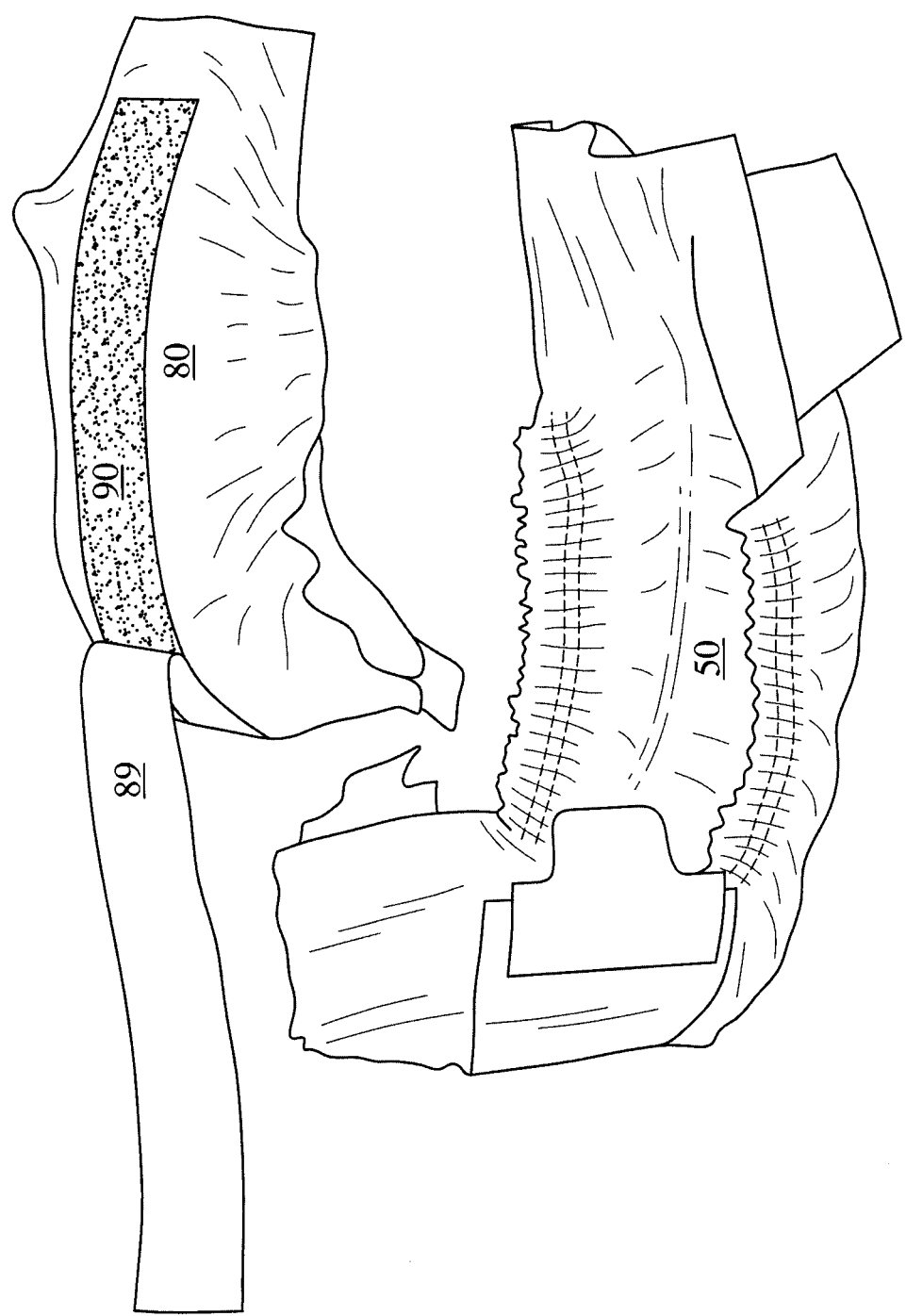
Figure 8:
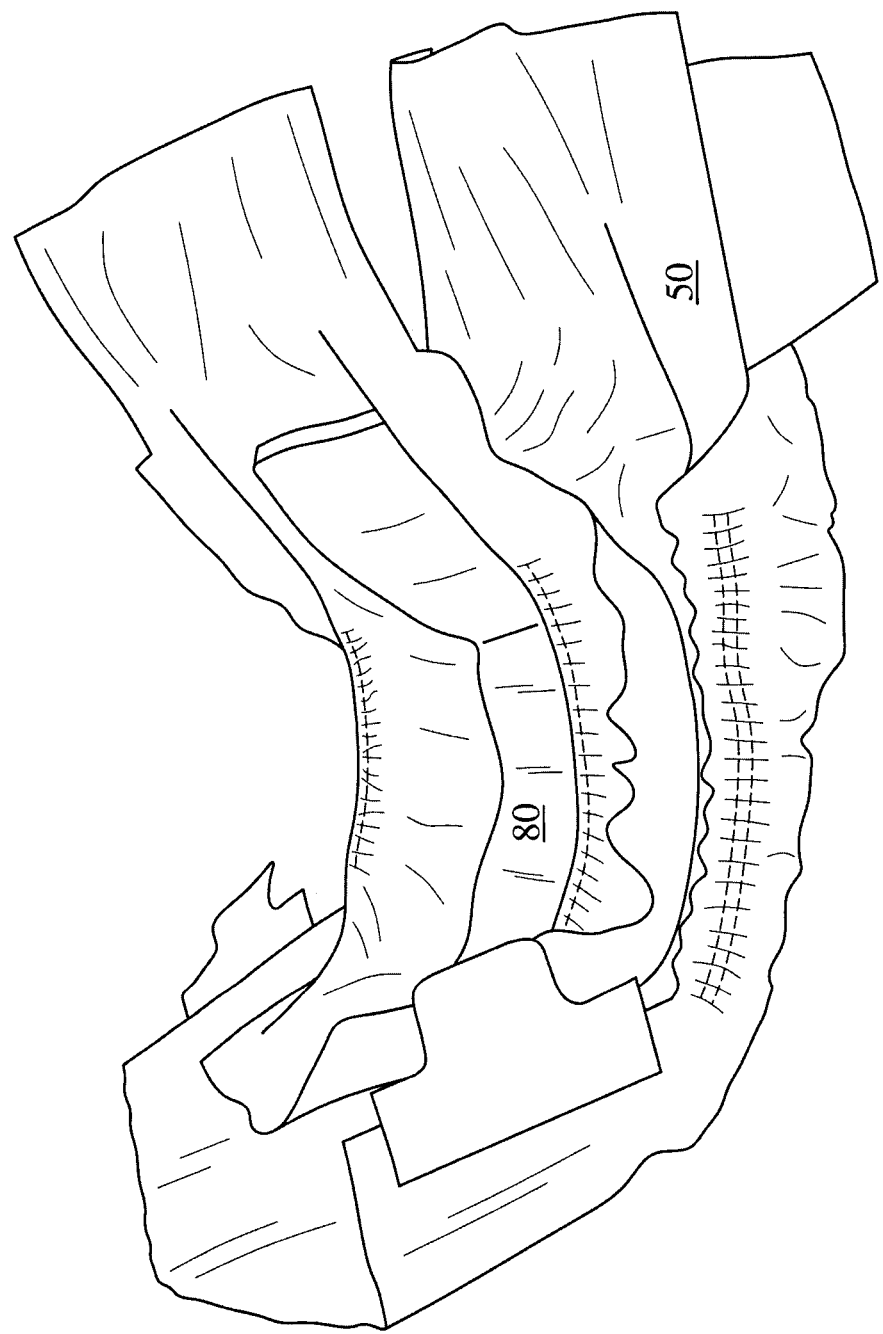
Figure 9:
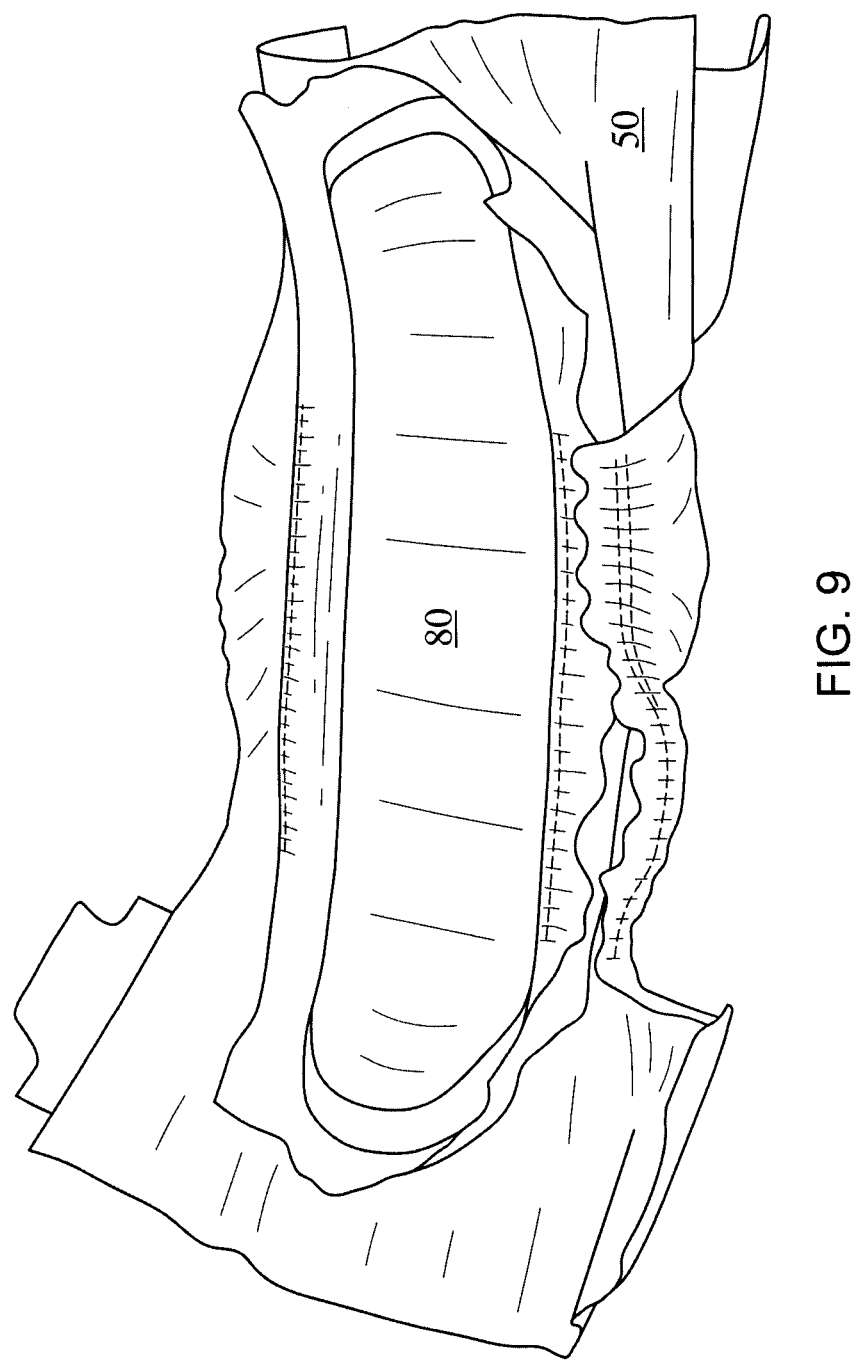
Figure 10:
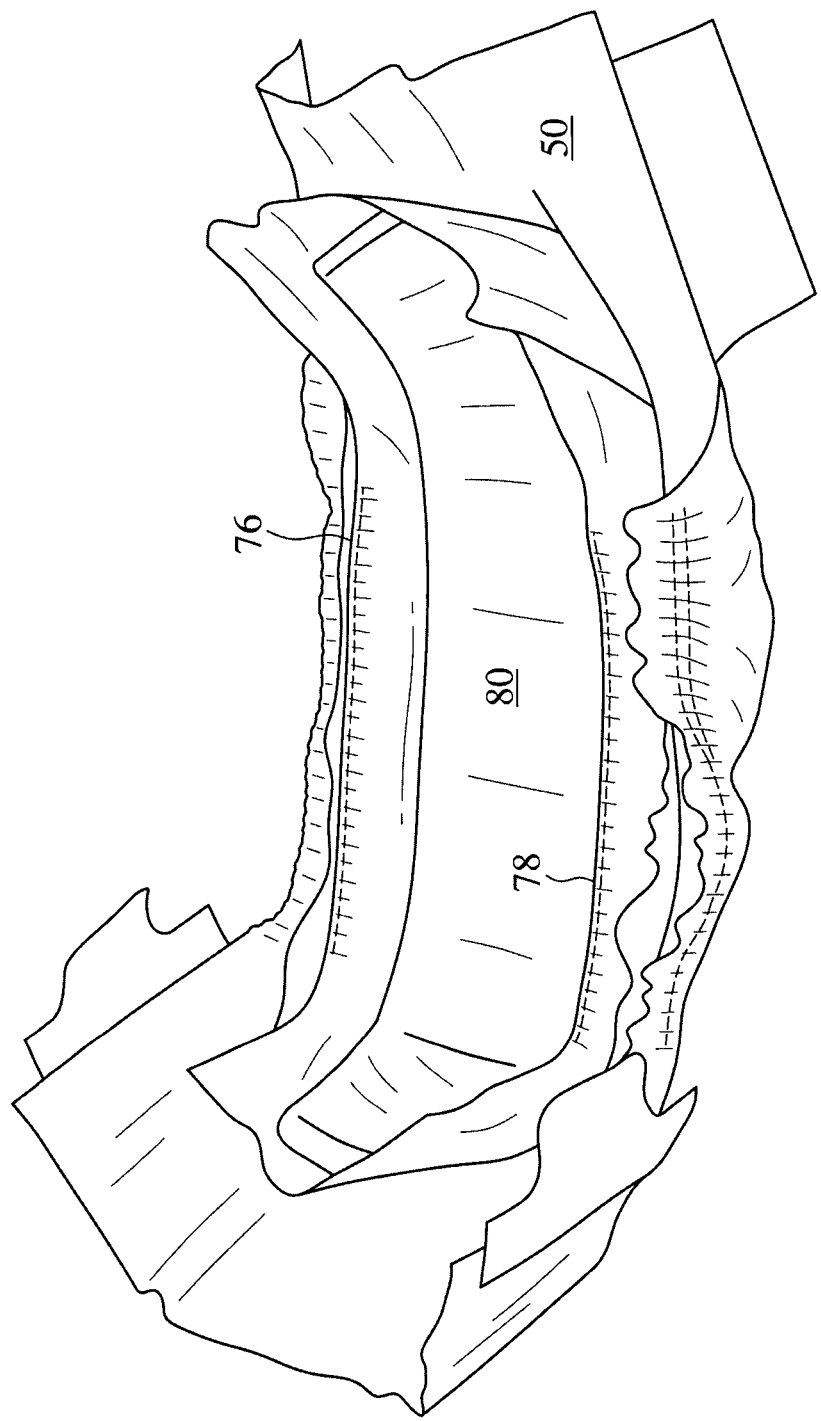
Figure 11:
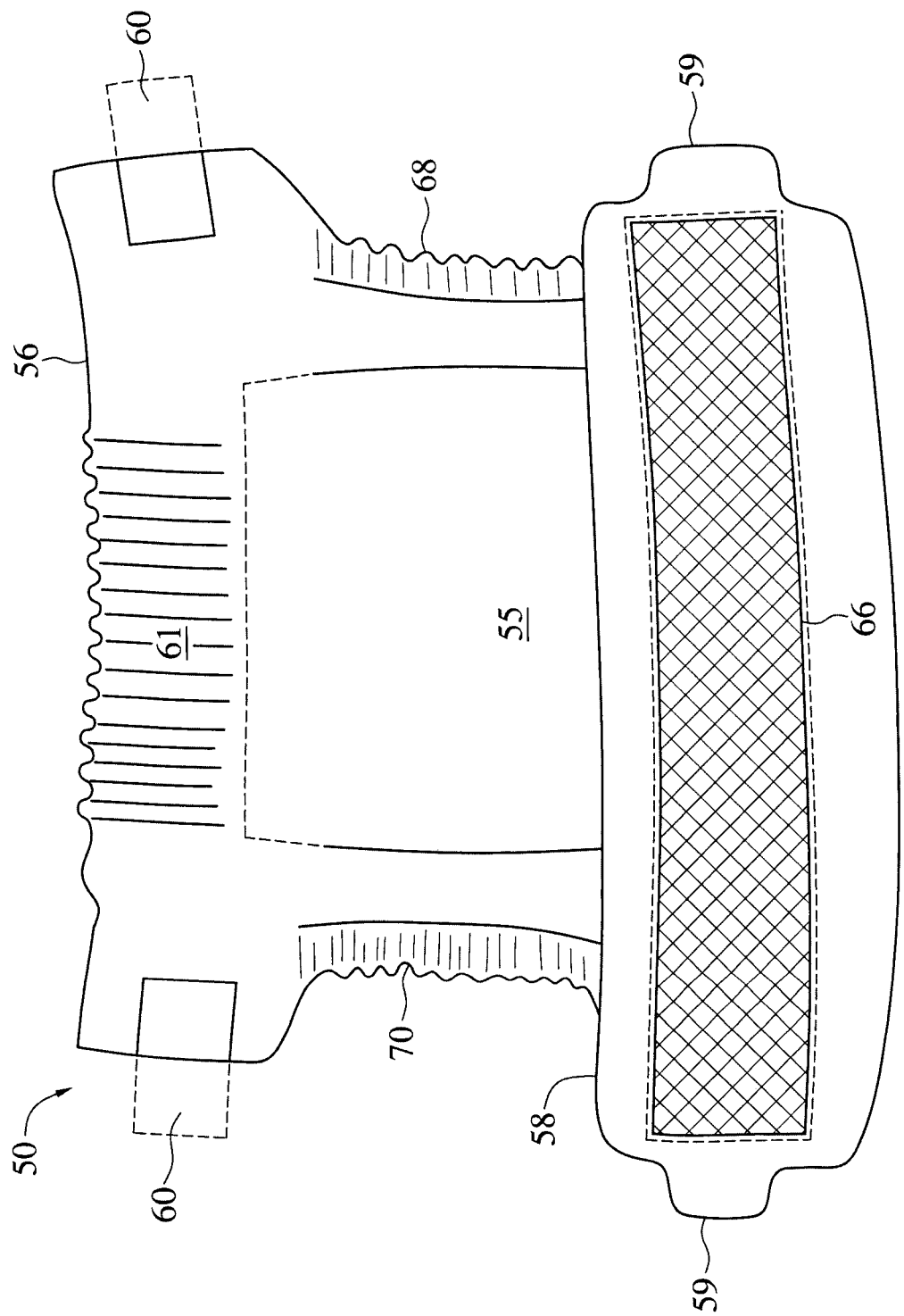
FIG. 11 is a front perspective view of a first embodiment of the re-usable non-absorbent diaper shell of the invention at rest, in a cupped configuration.
Figure 12:
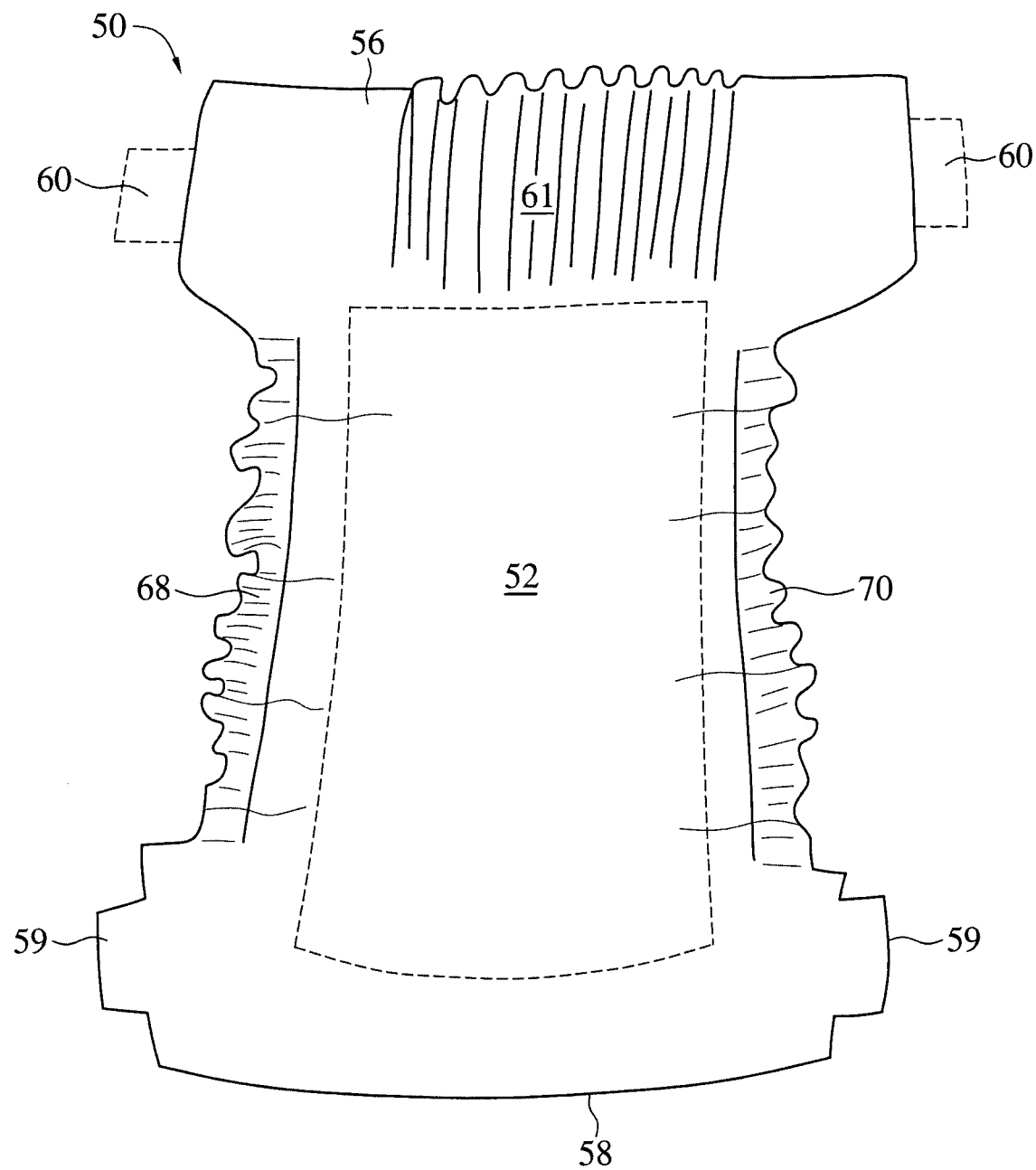
FIG. 12 is a rear perspective view of a first embodiment of the re-usable non-absorbent diaper shell as shown in FIG. 11.

To use the invention where the diaper channel is held by single-use disposable diaper 10 or shell 50, as shown in FIG. 7 (wherein the element designated 50 may be either a single-use disposable diaper 10 or shell 50) the user first removes release strip 89 to expose one or more strips of releasable adhesive 90, for example two parallel adhesive strips. The user then inserts channel 80 as shown between the leg cuffs of single-use disposable diaper 10 or shell 50. If a disposable diaper 10 with leg gathers is being used to hold channel insert diaper 80 it is preferable that the leg gathers 76, 78 on channel insert diaper 80 are higher than the leg gathers on the disposable diaper 10 to prevent the leg gathers on the disposable diaper from being soiled or wetted. The user will then apply the composite diaper system 50/80 to the infant in the usual way as with the conventional disposable diaper. After the channel insert diaper 80 has been wetted or soiled, it is removed from diaper 10 or shell 50 and replaced in diaper 10 or shell 50 with another channel insert diaper 80. Shell 50 can be rinsed or washed if necessary, before a replacement channel insert diaper 80 is inserted. After one or more replacement channel insert diapers 80 have been used and the diaper 10 has become soiled or the Velcro tabs no longer function, the single-use diaper 10 is disposed of. In this way, the single-use disposable diaper 10 may be re-used several or many times until the Velcro straps 28 are inoperative or the backsheet 12 itself is no longer intact or useable. At that point the diaper 10 can be discarded and a new diaper 10 used to receive the channel insert diaper 80. The channel insert diaper 80 is used in similar fashion with an underwear garment, swim pant, swim diaper or gPant™.

As described above a parent may choose to insert the channel insert diaper 80 into a standard single-use disposable diaper 10 to act as the absorbent pad and protect the disposable diaper from becoming wet or soiled, to thereby allow the parent to reduce waste by re-using the disposable diaper 10. In this way the channel insert diaper 80 acts as a diaper multiplier for single-use disposable diapers. Channel insert diaper 80 accomplishes this by the fact that it has a water impermeable back sheet and hydrophobic leg gathers to prevent waste from penetrating to the supporting disposable diaper.

FIG. 11 through 14 illustrate an embodiment of a reusable, disposable, rinsable and machine-washable diaper shell 50 for use with the present invention. The shell 50 comprises a water-impermeable backsheet 52 and a non-woven hydrophilic topsheet 54. Preferably the backsheet 52 is a breathable polyethylene (PE) layer laminated with a spunbond non woven layer 53. Preferably topsheet 54 is a polypropylene non-woven, particularly a spunbond melt-blown spunbond (SMS) spunbond non woven. The shell 50 has a back waist section 56, and front waist section 58. Flaps 60 attached to back waist section 56 have Velcro™ hook portion of strips 62 to attach the garment around the infant. Relatively weak adhesive strips are provided at 64 so the tabs 60 can be folded and held flat against the shell during washing so the Velcro does not attach to other articles during washing. Spandex elastic bands 61 are provided in the back waist section 56 to provide an elasticized waist band. A Velcro loop strip 66 is provided on the backsheet 52 in the front waist section 58 to which Velcro hook strips 62 can releasably adhere without tearing the backsheet 52 on removal. Tabs 59 can be provided to extend from either side of the front waist portion 58 to assist in guiding the shell 50 around the user's waist, and have an elastic strip 63 to provide additional stretch for the waist section 56. Outside elastic leg cuffs are provided at 68, 70 with elastic members 72 provided at their outer edges between back sheet 52 and top sheet 54. Elastic members 72 are typically thin rubber ribbons, or a hot melt elastomeric adhesive may be used as is known in the disposable diaper art.

Figure 13:
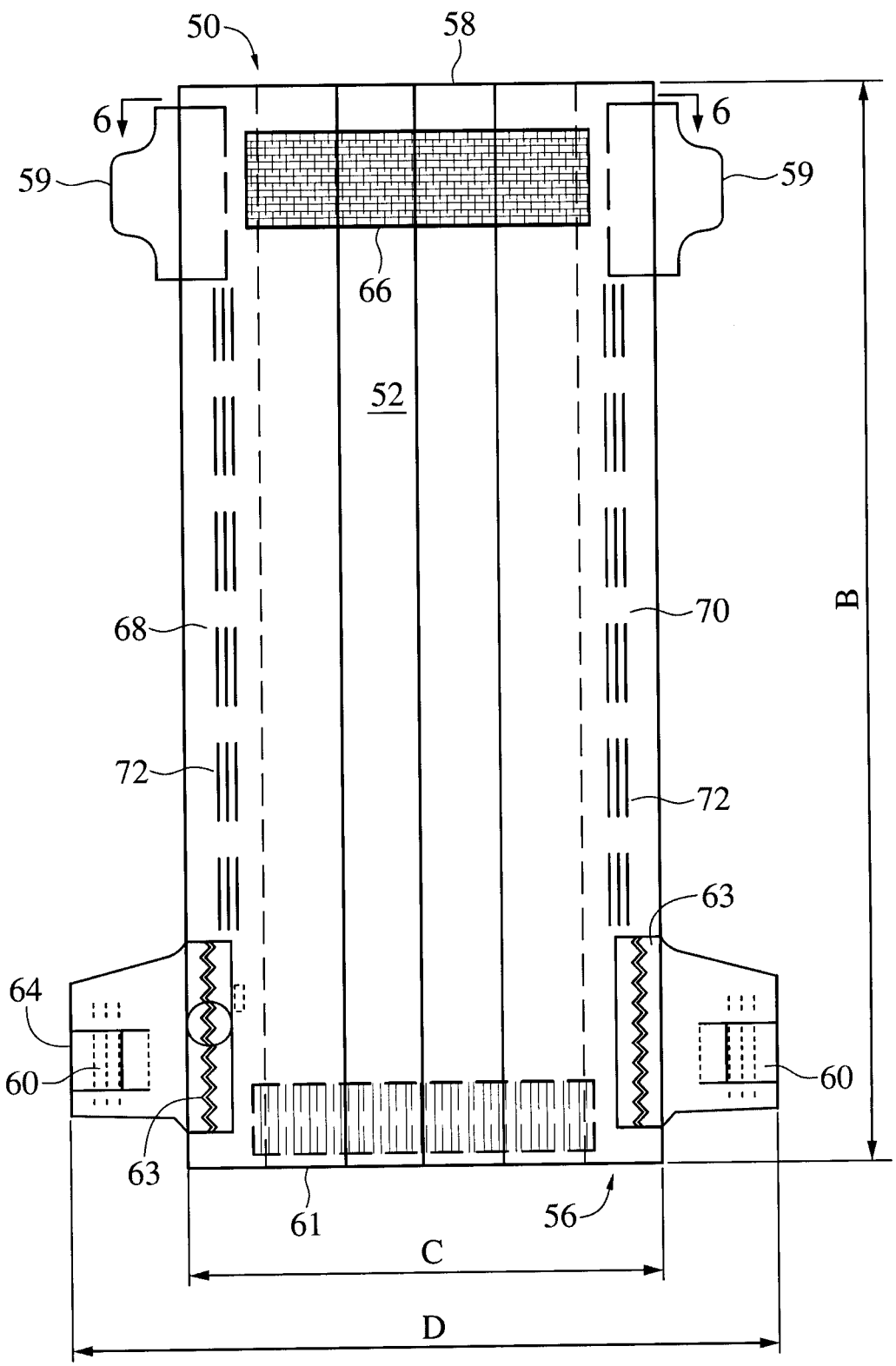
FIG. 13 is a plan view of the first embodiment of the re-usable non-absorbent diaper shell of the invention as shown in FIG. 11 in a flattened stretched configuration.
Figure 14:
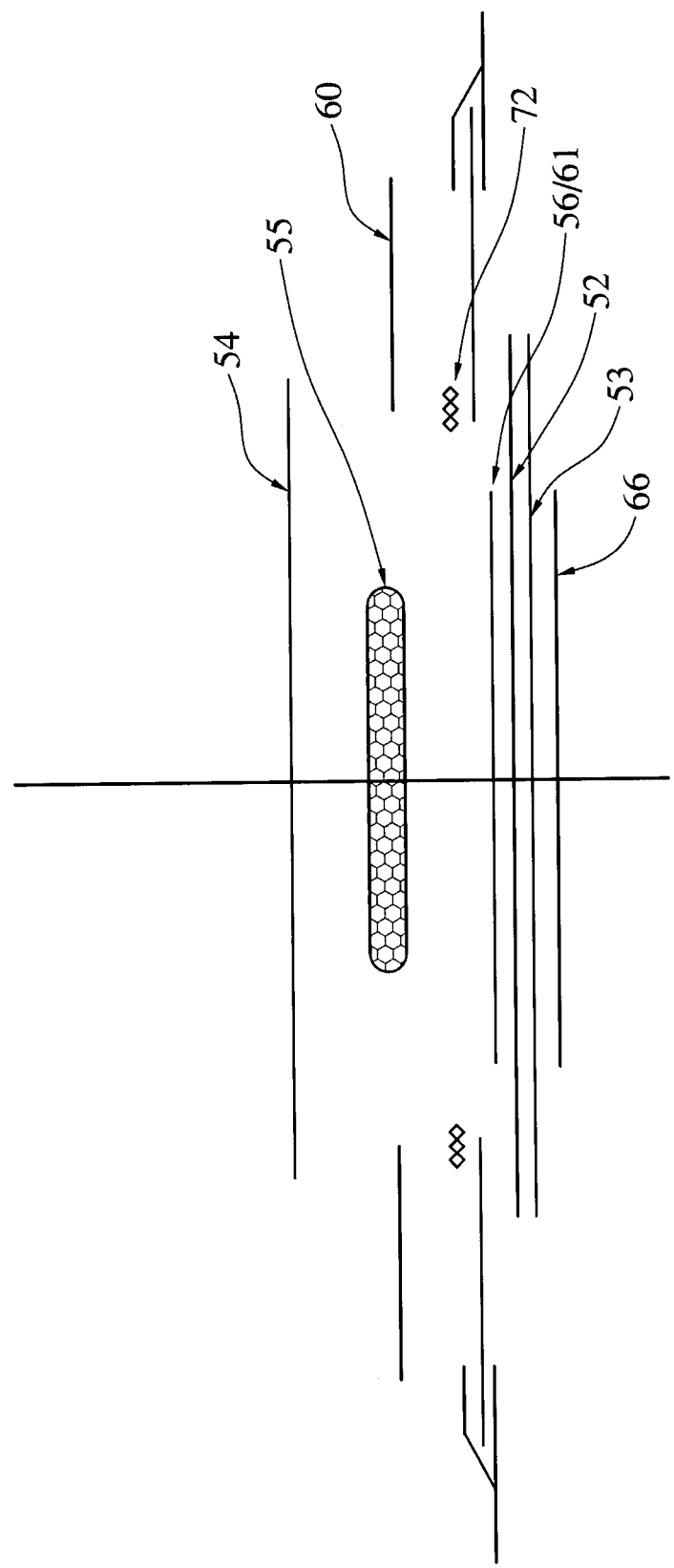
FIG. 14 is a cross-section taken along line 6-6 of FIG. 13 (not to scale).

A stabilizer strip 55 of spunbond non woven laminated with PE nonwoven laminated polethylene (PE) may be provided along the lengthwise central axis of diaper shell 50, laminated between the PE backsheet 52 and spunbond non woven topsheet 54. Stabilizing strip 55, which may be rectangular in shape, assists in stabilizing the shell 50 during the manufacturing and packaging process after the shell is cut to length, and facilitates the positioning and removal of a disposable replaceable absorbent insert within the shell 50, such as when a parent is replacing it in an infant diaper. The stabilizing strip 55 is narrower than the space between the leg cuffs 68, 70, as shown in FIG. 13, by a width X. By providing a stabilizer strip which is narrower than the separation of leg cuffs 68, 70, a deeper channel between the leg cuffs 68, 70 will be formed when the shell 50 is cupped for insertion of a diaper channel 80. In an embodiment of shell 50 which also includes leg gathers (not shown) located inwardly from leg cuffs 68, 70, the stabilizing strip 55 may also be narrower than the space between the leg gathers to provide a deeper channel to receive the absorbent insert.

The dimensions of the shell 50 will vary according to the size of the user of the garment, from newborn to adult. Examples of suitable dimensions for infant diapers are as follows. The length of stabilizer strip 55 may be the full length B of the shell 50, from 340 mm for a newborn size to 530 mm for an extra-large. The width of the stabilizer strip 55 may be 90 to 100 mm compared to the width C of the shell of 180 to 210 mm.

Other materials for the stabilizing strip 55 are possible, such as those described in PCT international application, publication no. WO 2008/014621 which is incorporated herein by reference. It may be a layer of flexible, resilient waterproof plastic material such as a closed cell, expanded low-density polyethylene referred to as PE foam from 1 to 5 mm in thickness, preferably about 2 mm thick. A suitable material for example is the PE foam underlayment sold by Goodfellow as 2.0 floating foam. The material for and thickness of the stabilizer strip 55 is selected so that it is soft and resilient in order to be comfortable for the baby, yet retains its shape when released. The material for and thickness of the stabilizer strip 55 is selected so that it provides the desired cupping of the shell 50 and opening and separation of the elastic leg cuffs 68, 70 to facilitate placement and removal of the absorbent diaper channel described below.

The stabilizer strip, for increased stiffness, may be formed as a textured layer having, for example, a stamped pattern providing a pattern of shallow raised edges or thickenings for strength, such as a cross-hatching, checkerboard or pattern of hollow circles, squares, rectangles, bubbles or other patterns for purposes of rigidity and baby comfort.

Shell 50 may be formed in a manner similar to the conventional disposable diaper 10, using conventional machinery for manufacturing disposable diapers, however no absorbent material exposed to the diaper interior is incorporated.

Existing machines for manufacturing disposable diapers, such as those manufactured by Fammeccanica, PCMC, Joa and Cellulose Converting Equipments, utilize a continuous line in which a ribbon of the absorbent layer is formed and shaped, and fed on a supporting surface such as tissue, the outer poly sheet is unwound from below the pulp line and adhesive and leg elastic are applied to it. The absorbent layer is then applied to the poly sheet, and a non-woven topsheet is applied over the absorbent layer and bonded to the poly back sheet, the elasticized leg gathers and tape tabs are applied and the diapers are then cut and folded. In the preferred method of manufacturing the present channel insert diaper, the channel insert diaper 80 may be manufactured in the same manner as conventional diapers but without including securement tabs, waist bands or elastic, and optionally without leg cuffs.

The disclosed embodiments may also improve the ability to recycle the used diapers. Currently disposable diapers are not easily recyclable. Currently suitable plastic films and absorbent pulp and SAPs all have potential applications for recycling. However due to difficulty in collecting and separating the potentially recyclable materials, recycling of disposable diapers is currently not widely accepted. The disclosed embodiments provide further advantages in facilitating the recycling of disposable diapers by providing multiple separate elements of the disposable diaper system. The present embodiments facilitate the separation of recyclable materials from a disposable diaper system. Different materials, such as plastic and SAP can be kept separated when the diaper is discarded because the diaper system is already a two piece system and is readily separated after use due to the use of releasable adhesive taping mechanisms. Further facilitation of recycling may be achieved using a three-piece system where the absorbent material such as the SAP is contained in the diaper channel in a separate releasable porous plastic pad/bag holder to facilitate separation and recycling after use. For example, where the supporting shell is a disposable re-usable machine-washable non-absorbent diaper shell, the supporting shell and diaper channel insert are separately collected for recycling of plastic and absorbent material. In that example the supporting shell is without absorbent material which is exposed to contact with liquid, the exterior shell is readily cleaned and prepared for recycling. As a further example the removable, replaceable disposable absorbent diaper channel's absorbent pad may be made separable from the body of the diaper channel for ease of separating and recycling the absorbent elements of the diaper channel. For example the SAP may be contained in a separable absorbent packet which can be separated from the diaper channel during the recycling process.

The foregoing description therefore describes how by using a disposable insert which takes the form of a diaper channel formed as a disposable diaper with a channel formed by interior leg gathers but no waist tabs or waist band and optionally without leg cuffs, which is referred to herein as a "channel insert diaper", the parent can convert a single-use diaper into a multiple-use diaper.

As will be apparent to those skilled in the art in the light of the foregoing disclosure, many alterations and modifications are possible in the practice of this invention without departing from the spirit or scope thereof. While the invention has been described in the context of an infant diaper it is also applicable to adult incontinence diapers and children's pull-ups. Thus while a number of exemplary aspects and embodiments have been discussed above, those of skill in the art will recognize certain modifications, permutations, additions and sub-combinations thereof.

What is claimed is:

1. A diapering system comprising:
   a) a conventional single-use disposable diaper comprising:
      i) a pliant liquid impervious body for removable fitting to the wearer, forming an interior and an exterior surface, a front and rear portion, opposed side edges and a crotch area when so fitted, and releasable waist tabs to secure said disposable diaper to the user;
      ii) opposed elastically contractible leg cuffs extending between the front and rear portion along said opposed side edges, the opposed elastically contractible leg cuffs thereby defining a central region between the opposed leg cuffs extending between the front and back portion; and b) a disposable absorbent channel insert diaper sized and configured to be removably inserted into said central region of said single-use disposable diaper, said disposable absorbent channel insert diaper constructed as a conventional disposable diaper having a front and rear portion with front and rear edges, a mid portion between said front and rear portions, opposed side edges and a crotch area when so fitted, but without waist tabs or waist band to secure the channel insert diaper to the user, and comprising (i) a water impermeable exterior backsheet,
(ii) a non-woven hydrophilic interior liner,
iii) an absorbent pad located between said backsheet and said interior liner wherein the upper surface of the absorbent pad is hydrophilic and
iv) two opposed hydrophobic elastic interior leg gathers extending lengthwise along either opposed edge thereof formed from hydrophobic non-woven sheets provided at an upper edge thereof with lengthwise extending elastic members wherein said elastic members are each connected at either end thereof to said backsheet, wherein lengthwise extents of said elastic members at rest are less than lengthwise extent of said channel insert diaper whereby said channel insert diaper forms a cupped shape defined by the front and rear portions being elevated relative to the mid portion.

2. The diapering system of claim 1 wherein each of said two opposed hydrophobic elastic interior leg gathers extending lengthwise along either opposed edge of said disposable absorbent channel insert diaper is spaced inwardly from said either opposed edge of said disposable absorbent channel insert diaper thereby providing a lengthwise strip of said exterior backsheet material between each said interior leg gather and said either opposed edge of said disposable absorbent channel insert diaper.

3. The diapering system of claim 1 wherein said elastic members of said disposable absorbent channel insert diaper are each connected at either end thereof to said backsheet at a point spaced downwardly from said front and rear edges and inwardly from each said opposed edge.

4. The diapering system of claim 1 in which the backsheet of said disposable absorbent channel insert diaper is provided on the outer surface thereof with one or more adhesive strips to removably secure said channel insert diaper to said single-use diaper.

5. The diapering system of claim 1 wherein said absorbent pad of said channel insert diaper comprises a super absorbent, super thin core.

6. A diapering system comprising: a plurality of channel insert diapers having the features described in claim 1 and at least one conventional single-use disposable diaper as described in claim 1.

7. In combination in a package, the diapering system of claim 6 comprising a plurality of said channel insert diapers and at least one conventional single-use disposable diaper.

8. A method of converting a conventional single-use disposable diaper into a multiple use diaper by multiplying the number of uses of the conventional single-use disposable diaper, said method comprising:

i) providing a first disposable absorbent channel insert diaper having the features described in claim 1, and a conventional single-use disposable diaper having the features described in claim 1;
ii) preparing said single-use disposable diaper for use in a first diapering event by inserting said first absorbent channel insert diaper into said single-use disposable diaper to form a first composite diaper;
iii) diapering said individual using said first composite diaper;
iv) when replacement of said first composite diaper is required by means of a second diapering event, disposing of said first absorbent channel insert diaper, taking any necessary steps to ensure said single-use diaper is sufficiently clean and intact, and replacing said first absorbent channel insert diaper with a second absorbent channel insert diaper to form a second composite diaper; and
v) repeating steps iii) and iv) as modified for third and subsequent diapering events until said single-use disposable diaper is no longer sufficiently clean or intact.

9. The method of claim 8 wherein each said channel insert diaper is provided with a separable super absorbent pulp (SAP) container and each said channel insert diaper is disposed of by recycling, comprising the further step of separating said SAP container from each said channel insert diaper when recycled.

* * * * *